(12) United States Patent
Lammle

(10) Patent No.: US 7,267,278 B2
(45) Date of Patent: Sep. 11, 2007

(54) METHOD AND SYSTEM FOR PROVIDING PHARMACEUTICAL PRODUCT INFORMATION TO A PATIENT

(76) Inventor: Robert Lammle, 2835 E. Pine View Dr., Salt Lake City, UT (US) 84121

( * ) Notice: Subject to any disclaimer, the term of this patent is extended or adjusted under 35 U.S.C. 154(b) by 0 days.

(21) Appl. No.: 10/602,138

(22) Filed: Jun. 23, 2003

(65) Prior Publication Data

US 2004/0256453 A1    Dec. 23, 2004

(51) Int. Cl.
*G06K 7/10* (2006.01)

(52) U.S. Cl. .................. 235/462.01; 235/375; 235/383; 235/472.02; 700/235; 340/5.25; 340/572.1; 705/2; 705/3; 705/10; 705/16; 705/26

(58) Field of Classification Search .......... 235/462.01, 235/375, 385, 383, 381, 472.02; 705/2–3, 705/10–16, 26; 340/5.25, 572.1; 700/236
See application file for complete search history.

(56) References Cited

U.S. PATENT DOCUMENTS

| | | | | |
|---|---|---|---|---|
| 5,353,121 | A * | 10/1994 | Young et al. | 725/52 |
| 5,442,390 | A * | 8/1995 | Hooper et al. | 725/90 |
| 5,867,821 | A * | 2/1999 | Ballantyne et al. | 705/2 |
| 6,067,524 | A * | 5/2000 | Byerly et al. | 705/3 |
| 6,193,154 | B1 * | 2/2001 | Phillips et al. | 235/381 |
| 6,202,923 | B1 * | 3/2001 | Boyer et al. | 235/375 |
| 6,240,394 | B1 * | 5/2001 | Uecker et al. | 705/3 |
| 6,692,436 | B1 * | 2/2004 | Bluth et al. | 600/300 |
| 2002/0022973 | A1 * | 2/2002 | Sun et al. | 705/3 |
| 2002/0143860 | A1 * | 10/2002 | Catan | 709/203 |
| 2003/0006878 | A1 * | 1/2003 | Chung | 340/5.25 |
| 2003/0018495 | A1 * | 1/2003 | Sussman | 705/2 |
| 2003/0112466 | A1 * | 6/2003 | Leonardi | 358/1.18 |
| 2003/0132298 | A1 * | 7/2003 | Swartz et al. | 235/472.02 |
| 2003/0183683 | A1 * | 10/2003 | Stewart | 235/376 |
| 2003/0191714 | A1 * | 10/2003 | Norris | 705/43 |
| 2004/0015395 | A1 * | 1/2004 | Acosta | 705/14 |
| 2004/0059624 | A1 * | 3/2004 | Wantulok et al. | 705/10 |
| 2004/0065739 | A1 * | 4/2004 | Xu et al. | 235/462.1 |
| 2004/0068421 | A1 * | 4/2004 | Drapeau et al. | 705/2 |
| 2004/0078218 | A1 * | 4/2004 | Badinelli | 705/2 |

(Continued)

OTHER PUBLICATIONS

Felkey, Bill G., et al., "Development of a Visualized Drug Information Database for United States Pharmacopeia Dispensing Information," Drug Information Journal, vol. 29, pp. 1727S-1741S (1995), no month.

*Primary Examiner*—Michael G. Lee
*Assistant Examiner*—Allyson N Trail
(74) *Attorney, Agent, or Firm*—TraskBritt

(57) ABSTRACT

A system and method for providing pharmaceutical information to a patient is disclosed. The invention includes electronically identifying the pharmaceutical product dispensed to the patient with an identification device and electronically prompting the patient with a message using a first output. The message provides the patient with the opportunity to accept or decline the pharmaceutical information by interacting with an input device. If the patient decides to accept the pharmaceutical information, the pharmaceutical information is provided to the patient through a second output. A computer-based apparatus is also disclosed for providing pharmaceutical information to the patient. The computer-based apparatus includes a central processing unit configured to run an executable software program configured to control the functions of peripheral devices operatively connected to the computer-based apparatus.

10 Claims, 4 Drawing Sheets

U.S. PATENT DOCUMENTS

2004/0078237 A1* 4/2004 Kaafarani et al. ............. 705/2
2004/0081669 A1* 4/2004 Greeven et al. ............ 424/400
2004/0210341 A1* 10/2004 Wallace et al. ............. 700/237
2004/0215369 A1* 10/2004 Rosenblum ................. 700/235
2005/0021175 A1* 1/2005 Bain ........................... 700/236

* cited by examiner

METHOD AND SYSTEM FOR PROVIDING PHARMACEUTICAL PRODUCT INFORMATION TO A PATIENT

TECHNICAL FIELD

The present invention relates generally to interactive user systems and more particularly, to interactive user systems structured and designed to deliver pharmaceutical product instructions and information to patients.

BACKGROUND

Over the past 10 years, the pharmaceutical industry has undergone a great deal of change in response to the numerous changes that have affected the health care industry. In response to these changes, the role of the pharmacist, as well as the entire practice of pharmacy, has changed.

As a result of the changes in the health care industry, the rate at which prescriptions are filled is continually on the rise. For instance, in the year 2001, there were more than 3 billion prescriptions filled according to the Schering Report XXIII: Pharmacists, Technicians and Technology: Serving the Patient (hereinafter "the Schering Report"). At the current rate, there is estimated to be over 4 billion prescriptions filled in the year 2004. As there are just over 50,000 pharmacies in the United States, including specialty programs such as nursing homes, institutional pharmacies and hospital pharmacies, the number of prescriptions filled each hour, by each pharmacy, is about 20 prescriptions.

In addition to the growing number of prescriptions, the number of unfilled pharmacist vacancies has nearly tripled in two years according to a report issued by the U.S. Department of Health and Human Services in December of 2000. Further, according to statistics provided by the National Association of Chain Drug Stores, there were approximately 6,503 open pharmacy positions as of January, 2002. Combining the number of unfilled pharmacist vacancies with the fact that the number of newly graduating pharmacists has declined in recent years, it is apparent that there is becoming a nationwide shortage of full-time pharmacists. Due to the increased demand and shortened supply of pharmacists, pharmacists may earn between about $80,000 to $100,000 annually.

In addition to paying higher salaries, pharmacy profit margins have also been decreasing. This decrease has resulted in the number of independent pharmacies (not affiliated with a chain store or mass merchandiser) to decline from about 30,503 in 1991 to 20,647 in 2001. Decreased profitability is attributable not only to increasing overhead costs, but also due to the overall business mix, including a larger percentage of third party prescriptions. Depending on the geographical location of the pharmacy, the percentage of third party prescriptions filled by the pharmacy (paid by an insurer or Medicaid/Medicare) ranged from 67 to 100 percent, with an average of 83 percent according to the National Association of Chain Drug Stores, Industry Statistics, 2002. Since the third party payer often allocates a maximum allowable cost per prescription, mandatory generic prescriptions, network discounts and prior authorizations, the amount of money the third party payor pays the pharmacy affects the profit margin of the pharmacy.

Concomitantly, the duties on each pharmacist are also increasing. For instance, the pharmacist not only takes the prescription order, commits the order to writing when called by a physician, consults with physicians and nurses on proper medication and doses, processes the prescription, checks for drug-drug interactions, obtains the proper medication, measures the quantity of the medication, fills the prescription, affixes a label to the prescription and completes the proper financial transaction to check the patient out of the pharmacy, the pharmacist also needs to counsel the patient. Patient counseling helps to ensure that the patient properly understands instructions on how to take the medication or use a pharmaceutical product such that that the medication or pharmaceutical product works optimally. In addition to filling prescriptions, the pharmacist also attends to a daily barrage of questions regarding over-the-counter medications and other pharmaceutical products that have increased in availability and complexity.

Most pharmacies provide services to Medicaid and Medicare patients and thus are subject to the Omnibus Reconciliation Act passed in 1990 (OBRA) which mandates that each Medicaid and Medicare patient receive the following information when getting a prescription: the name of the medication, the description of the medication, the dosage form, the dosage, how to administer the medication, the duration of the drug therapy, and how to handle missed doses. Additionally, almost every state requires that the patient be offered counseling on the prescription in which the above listed information is communicated by the pharmacist. Some states allow ancillary pharmacy staff to provide the counseling information, but other states require the pharmacist to personally counsel the patient.

Since most pharmacists are quite busy, pharmacies often use ancillary support staff to perform clerical duties and other functions. The number of support staff available to pharmacies is often limited by the states to a 2:1 or a 3:1 ratio of support staff to each pharmacist. Although the ancillary pharmacy staff perform a number functions to assist the pharmacist, patient counseling remains a duty relegated to the pharmacist. Although patients picking up refills typically refuse counseling at the point-of-sale (POS), according to the Schering report, pharmacists indicate that they counsel about 90-100% of patients that are picking up new prescriptions. Further complicating the ability of the pharmacist to counsel patients is the fact that compliance with managed health care and third party payor paperwork requirements adds more time to the prescription process. In a survey, about 75% of pharmacists and pharmacy technicians report spending about a third of their time dealing with paperwork, phone calls and other activities to resolve third-party and drug-benefit issues according to the Schering Report.

The pharmacist and the ancillary pharmacy staff are left with a small portion of time to counsel patients on the use of medications. Thus, the effectiveness of a drug's therapy may be jeopardized if the patient does not take the medication properly and the pharmacist does not have enough time to counsel the patient properly. For instance, it is estimated that between 30 and 50% of patients fail to comply with prescription instructions according to the article "A Pharmacist's Duty to Warn: Sound Economics, Effective Medicine and Consistent with Drug Regulation Theory" by Harit V. Trivedi, Harvard Law School, 1995.

Over the years, a number of innovations have been developed to reduce the pharmacist's workload, reduce costs and provide added value to customers in an effort to increase the efficiency of the practice of pharmacy. These innovations include centralized processing of third-party prescriptions, electronic prescribing, standardized pharmacy benefit cards, access to patient specific clinical information, in-pharmacy telephones that may be used by patients to call their doctor for refills, menu-driven interactive voice-response systems for refills and other information, and the ability to order refills on the internet. Electronic prescribing and standardized drug benefit cards focus on reducing the paperwork or administrative workload within the pharmacy. However, not all of these innovations are logistically practical and few of the innovations focus on reducing the counseling workload of the pharmacist. Furthermore, although in-pharmacy telephone interactive response systems and internet refills help ease the workload on the pharmacy, these innovations do not necessarily help provide the required counseling. Even though the innovations may increase the number of prescriptions filled each hour, the innovations do not help the pharmacist counsel the patient or explain pharmaceutical product information more effectively. Also, some of the innovations are still in the development stages and may be difficult or impractical to implement.

SUMMARY OF THE INVENTION

In accordance with the invention, a method for providing pharmaceutical information interactively to a patient is disclosed. The method includes identifying a pharmaceutical product dispensed to the patient and prompting the patient with a computer generated message which provides the patient with an opportunity to accept or decline the interactive pharmaceutical information. An input device located within the pharmacy is provided which allows the patient to accept or decline the interactive pharmaceutical information by interacting with the input device. If the patient opts to accept pharmaceutical information, the interactive pharmaceutical information is automatically provided to the patient.

An in-pharmacy system for providing interactive pharmaceutical information to a patient is also disclosed. The system includes an electronic identification device for determining a medication in a pharmaceutical product and a first computerized output for communicating a message to the patient. An input system for interacting with the patient is also provided. The system further includes a second output system for providing the pharmaceutical information to the patient.

The invention further discloses a computer-based system for storing, retrieving and disclosing interactive pharmaceutical information to a patient. The computer-based system includes a first peripheral information identification device for identifying a medication in a pharmaceutical product and a display for visually or audibly communicating a message to the patient. An input device for interacting with the patient and an output device for disclosing the pharmaceutical information to the patient are also disclosed. The computer-based system further includes a central processing unit configured to run at least one executable software program, wherein the at least one executable software program is stored on at least one memory device of the central processing unit. At least partially in response to the executable software program, the central processing unit controls the function of the first peripheral device, the display, the input device, and the output.

BRIEF DESCRIPTION OF THE DRAWINGS

While the specification concludes with claims particularly pointing out and distinctly claiming that which is regarded as the present invention, the invention can be more readily ascertained from the following description of the invention when read in conjunction with the accompanying drawings in which:

DETAILED DESCRIPTION

In the following detailed description, the following definitions will be used to more clearly define the invention. The phrase "pharmaceutical information" will be used, generally, to refer to information pertaining to a prescription or other pharmaceutical product. The information may be provided orally, in a printed paper form, visually on an electronic display or combinations thereof. The pharmaceutical information may include, but is not limited to, the name of the pharmaceutical product, the description of the pharmaceutical product, the dosage form, the dosage, how to administer the pharmaceutical product, the duration of the drug therapy, and how to handle missed doses. The term "pharmaceutical instructions" will be used to refer to directions, advice and other recommendations provided to the patient on how to use the pharmaceutical product or prescription and other related information. As used herein, the term "patient" will be used to refer to any person or subject that receives the pharmaceutical instructions and is not limited to a person under the care of a physician. The term "patient" also refers to a person picking the pharmaceutical instructions for another person, such as a parent or a guardian picking up the pharmaceutical instructions for a child or another person. The "pharmaceutical instructions" may include prescription counseling provided directly to the patient through pharmacist-patient interaction or indirectly to the patient by pharmacist-patient interaction through a computer-based system, telephone system or other electronic system.

As known by those of ordinary skill in the art, after a patient receives a prescription from a doctor, the patient typically visits a pharmacy to have the prescription filled. The patient typically receives pharmaceutical product information related to the prescription in addition to the filled prescription and the pharmacy may be required to offer pharmaceutical instructions to the patient in accordance with state law, along with a credible record of each event.

Figure 1:
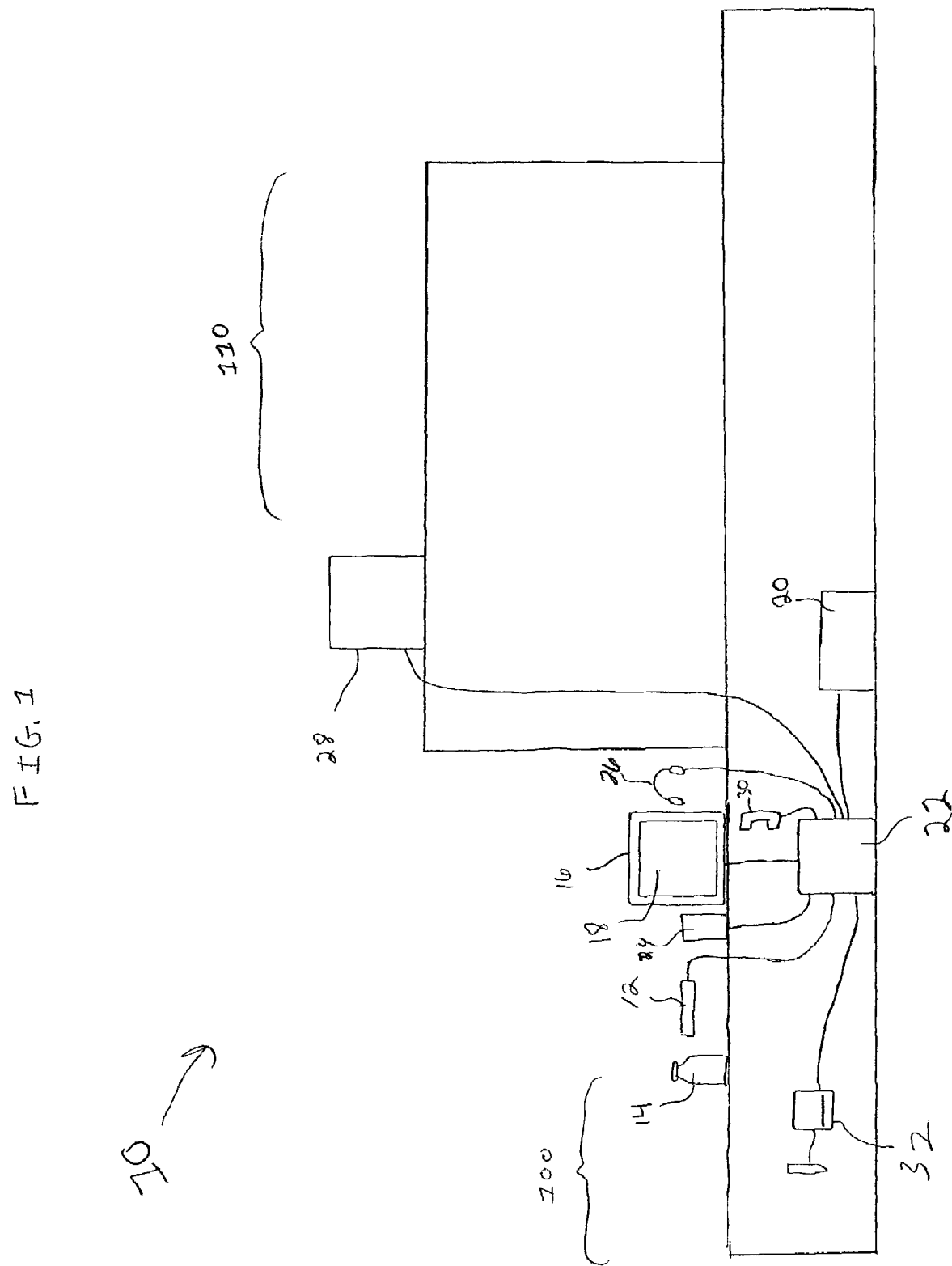
FIG. 1 is a schematic representation of a pharmaceutical information system.

Referring now to FIG. 1, there is shown a pharmaceutical instruction system of the present invention generally at 10. The pharmaceutical instruction system (hereinafter "instruction system") 10 includes an identification device 12 for identifying a pharmaceutical product 14, such as a prescription. In the illustrated embodiment, the identification device 12 is a bar-code scanner, although the identification device 12 may be a magnetic strip scanner or similar device. The pharmaceutical instruction system 10 also includes a display 16 which serves to communicate visually pharmaceutical product information and other types of information to a patient (not shown). In the illustrated embodiment, the display 16 is a touch-sensitive screen 18 which allows the patient to interact with the pharmaceutical instruction system. A printer 20 is also provided within the pharmaceutical instruction system 10 for printing the pharmaceutical product information on a print medium, such as paper, for delivery to the patient.

In an alternative embodiment, the display 16 may comprise a screen with attached yes and no buttons that allows a patient, or other user of the pharmaceutical instruction system 10, to interact with the pharmaceutical instruction system 10 by simply pressing the yes or no button.

As illustrated, the pharmaceutical instruction system 10 includes a notification device 28 for informing the pharmacist, or ancillary pharmacy staff, of actions taken by the patient. The notification device 28 is located in a pharmacist area 110 where the pharmacist may view the notification device 28 during the normal course of the pharmacist's duties, and in the illustrated embodiment is a computer monitor. A computer-based apparatus 22 is operatively connected to the various peripheral devices of the pharmaceutical instruction system 10 and functions to control the various peripheral devices. In the illustrated embodiment, the computer-based apparatus 22 is a computer system, such as a personal computer or computer work station. As known in the art, the computer-based apparatus 22 may comprise any other type of known computer system. Further, the computer-based apparatus 22 may be operatively connected to a local area network, a wide area network or the Internet.

Figure 2:
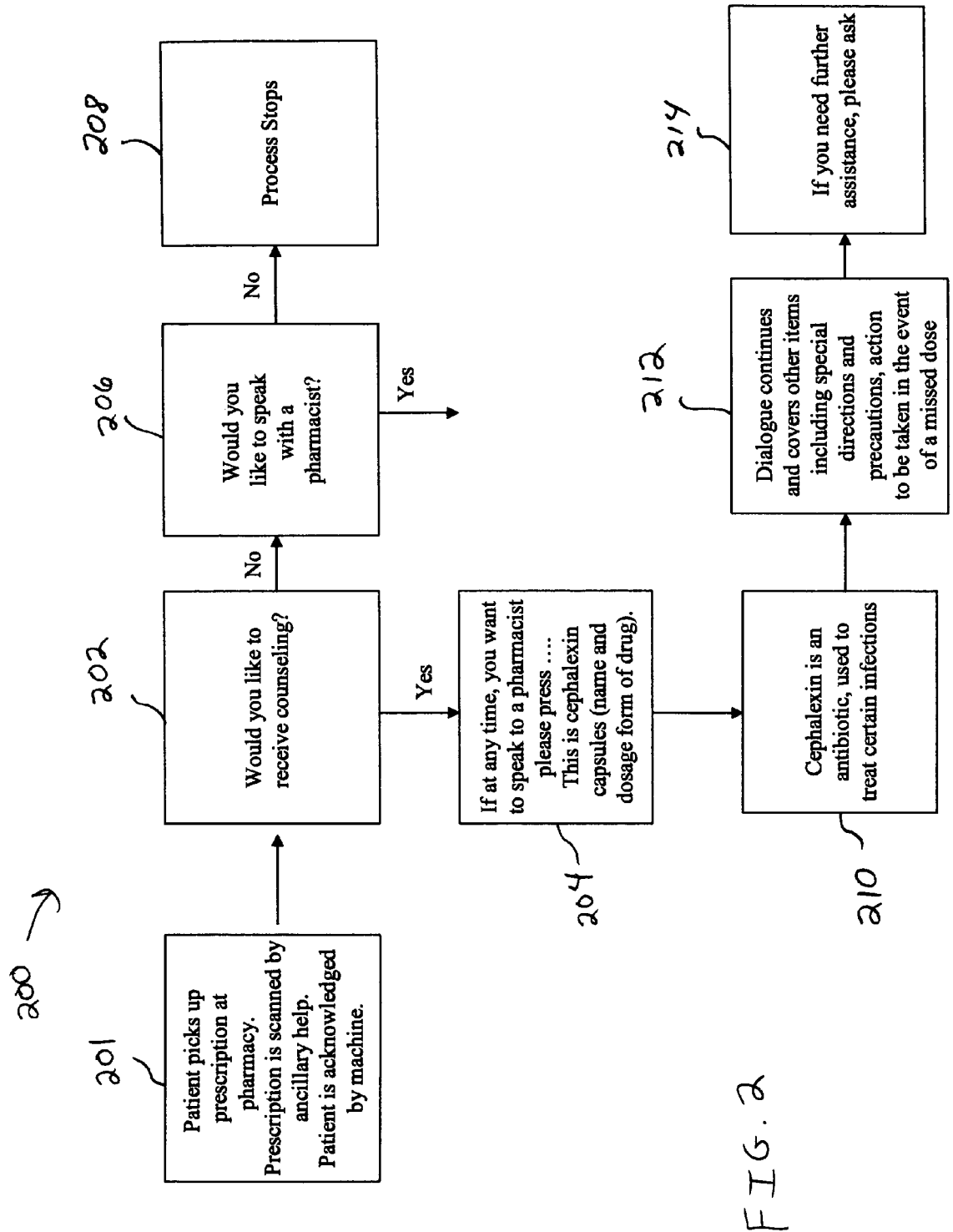
FIG. 2 depicts a flowchart of a method of providing pharmaceutical instruction and information to a patient.

The pharmaceutical information system 10 is used to provide pharmaceutical information to a patient. Referring to FIG. 2, there is shown a flow chart illustrating a method for providing pharmaceutical information to the patient generally at 200. Referring in conjunction to FIG. 1 and FIG. 2, the patient takes a prescription obtained from a doctor to a point-of-sale area 100 of a pharmacy. After the pharmacist fills the prescription, the patient picks up the filled prescription, the pharmaceutical product 14, in the vicinity of the point-of-sale area 100 within the pharmacy.

When pharmacy personnel, such as the pharmacist or an ancillary staff member of the pharmacy, deliver the pharmaceutical product 14 to the patient, an electronically readable identification tag on the pharmaceutical product 14 is electronically identified at step 201. In one embodiment, the electronically readable identification tag is a bar code on the pharmaceutical product 14 and is scanned with the bar-code scanner 12. Bar code scanners are well known by those of ordinary skill in the art. The bar code of the pharmaceutical product 14 may be a National Drug Code (NDC) for the particular medication, a proprietary code of the pharmacy, a Universal Product Code (UPC) symbol, or any other merchandising code known by those of ordinary skill in the art. In alternative embodiments, the identification device 12 may comprise any other type of scanning system that electronically identifies the electronically readable identification tag on the pharmaceutical product such as magnetic strip readers, radio frequency identification tags, laser readable tags, infrared readable tags or any other identification system or device known by those of ordinary skill in the art. In alternative embodiments, the identification device 12 may be replaced by a keyboard or similar input device which allows the pharmacy personnel to manually enter the type of medication into the pharmaceutical instruction system 10.

Once the pharmaceutical product 14 is identified, the patient is prompted with a first electronic message generated by the computer-based apparatus 22 of the pharmaceutical instruction system 10 at step 202. The first electronic message is conveyed to the patient, such as on the touch screen 18 of the display 16. The first electronic message may recite "Would you like to receive information regarding the pharmaceutical product?" or other equivalent message. In alternative embodiments, the first electronic message may be communicated to the patient using a regular computer monitor as the display, by an audible communication through a speaker, by being spoken by the pharmacy staff or in any other known manner.

In an alternative embodiment, once the pharmaceutical product 14 is identified, the instruction system 10 may be operatively configured to electronically convey, i.e., audibly, visually or a combination thereof, to the patient what type of pharmaceutical product 14 has been identified. For instance, if the pharmaceutical product is a prescription, a message conveyed to the patient may recite "You have been prescribed an antibiotic" or any other equivalent message. In this manner, the patient will be able to ascertain whether or not they are receiving the proper pharmaceutical product.

Figure 3:
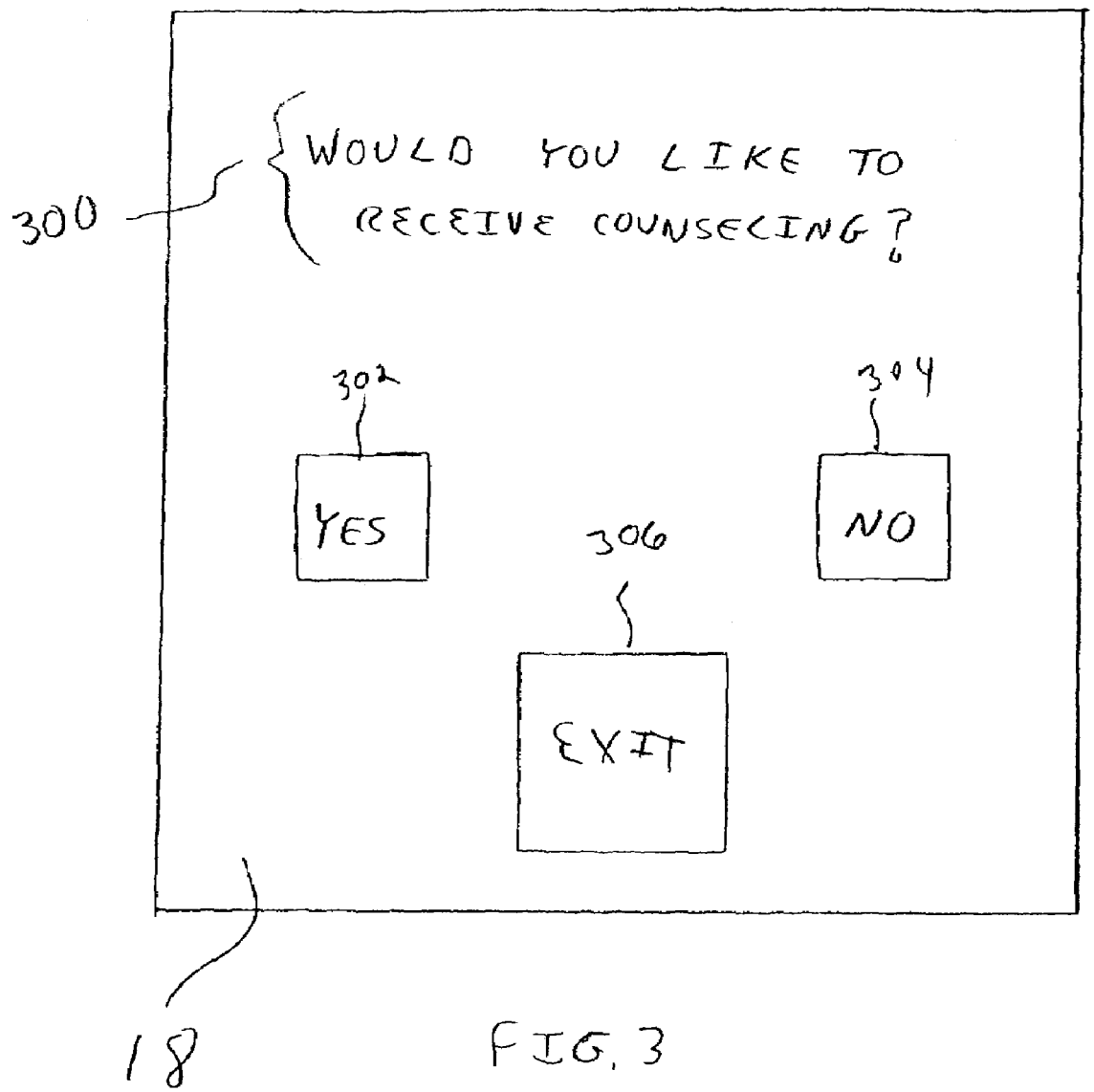
FIG. 3 is an expanded view of the touch-screen of FIG. 1.

Referring now to FIG. 3, there is illustrated a close-up view of the touch screen 18. As illustrated in FIG. 3, the first electronic message "Would you like to receive information regarding the pharmaceutical product?" is displayed to the patient at bracket 300. After viewing the first electronic message, the patient is provided with the opportunity to accept or decline the pharmaceutical information. If the patient wishes to accept pharmaceutical information, the patient touches the "YES" icon 302 on the touch screen 18. Touch screens 18 are well known by those of ordinary skill in the art and are configured to sense touching of the screen such that the patient may interact with the pharmaceutical instruction system 10 by touching the touch screen 18. If the patient wishes to decline pharmaceutical information, the patient touches the "NO" icon 304 of the touch screen 18 of FIG. 3. If the patient rejects pharmaceutical information, the process stops and the transaction is complete.

Although the illustrated embodiment depicts the use of a touch screen 18 as an input device, it will be apparent by those of ordinary skill in the art that any other input device which performs functions the same as or equivalent to the touch screen 18 described herein are meant to be encompassed by the present invention. For instance, the pharmaceutical instruction system 10 may include a mouse, a keyboard, a voice activated recognition system, a set of yes and no keys, any other type of known input device or combinations thereof which allows the patient to interact with the pharmaceutical instruction system 10.

Referring again to FIG. 2, if the patient opts to receive pharmaceutical information, the touch screen 18 displays pharmaceutical information options to the patient and "walks" the patient through elements of the pharmaceutical information. For instance, at step 204 the patient is informed about one aspect of the pharmaceutical product. The patient may be "walked" through various screens displaying the pharmaceutical product information where the patient is provided with additional opportunities to learn more about particular aspects of the medication, move on to the next screen, or have the opportunity to opt out of the instruction program at any time and speak with the pharmacist by interacting with the touch screen 18. For instance, if the pharmaceutical instruction system 10 were operatively connected to the Internet, the pharmaceutical instruction system 10 may enable the patient to view pharmaceutical product information from a web-site of the manufacturer of the pharmaceutical product.

In the illustrated embodiment, the patient is informed that the pharmaceutical product includes, for example, cephalexin capsules at step 204. At this point, the patient may be provided with another opportunity to continue receiving pharmaceutical information or to quit receiving pharmaceutical information by touching an appropriate icon on the touch screen 18. If the patient continues receiving pharmaceutical information, the patient may be provided with additional information about the cephalexin antibiotic at step 210. The patient may also be provided with the option to continue receiving pharmaceutical information or quit receiving pharmaceutical information at step 210 by interacting with the touch-screen 18 and selecting the appropriate icon. If the patient opts to continue receiving pharmaceutical information, the patient may be provided with additional information including special directions, precautions, other drug interactions, adverse side effects and the action to be taken in the event a dose is missed at step 212. Once the pharmaceutical information ends, the patient may be prompted to ask for further assistance, speak with the pharmacist or end the pharmaceutical information session at step 214.

As illustrated in FIG. 1, the touch screen 18 is used to provide pharmaceutical information to the patient. It will be appreciated by those of ordinary skill in the art that other output devices may be used in combination with, or in place of, the touch screen 18. For instance, the patient may receive pharmaceutical information orally through a speaker 24, through a set of headphones 26 or a telephone receiver 30. If the patient receives the pharmaceutical information orally, a digitized voice simulation may be provided with the computer-based apparatus 22 and configured to present the pharmaceutical information at a volume level consistent with normal hearing. Alternatively, if the patient is hearing impaired, the patient may be able to use the headphones 26 or telephone receiver 30 and amplify the volume to assist the patient. By using the headphones 26 or the telephone receiver 30, the patient is able to receive the pharmaceutical information without being overheard by other people at the pharmacy which is consistent with HIPPA which desires to achieve patient confidentiality.

Alternatively, the printer 20 may be used to print the pharmaceutical information on print medium, such as paper, where the patient may take the pharmaceutical information with him or her to read at his or her convenience. In another embodiment where the pharmaceutical instruction system 10 is operatively connected to the Internet, the patient may have the option of having the pharmaceutical product information sent to an email account for the convenience of the patient.

Figure 4:
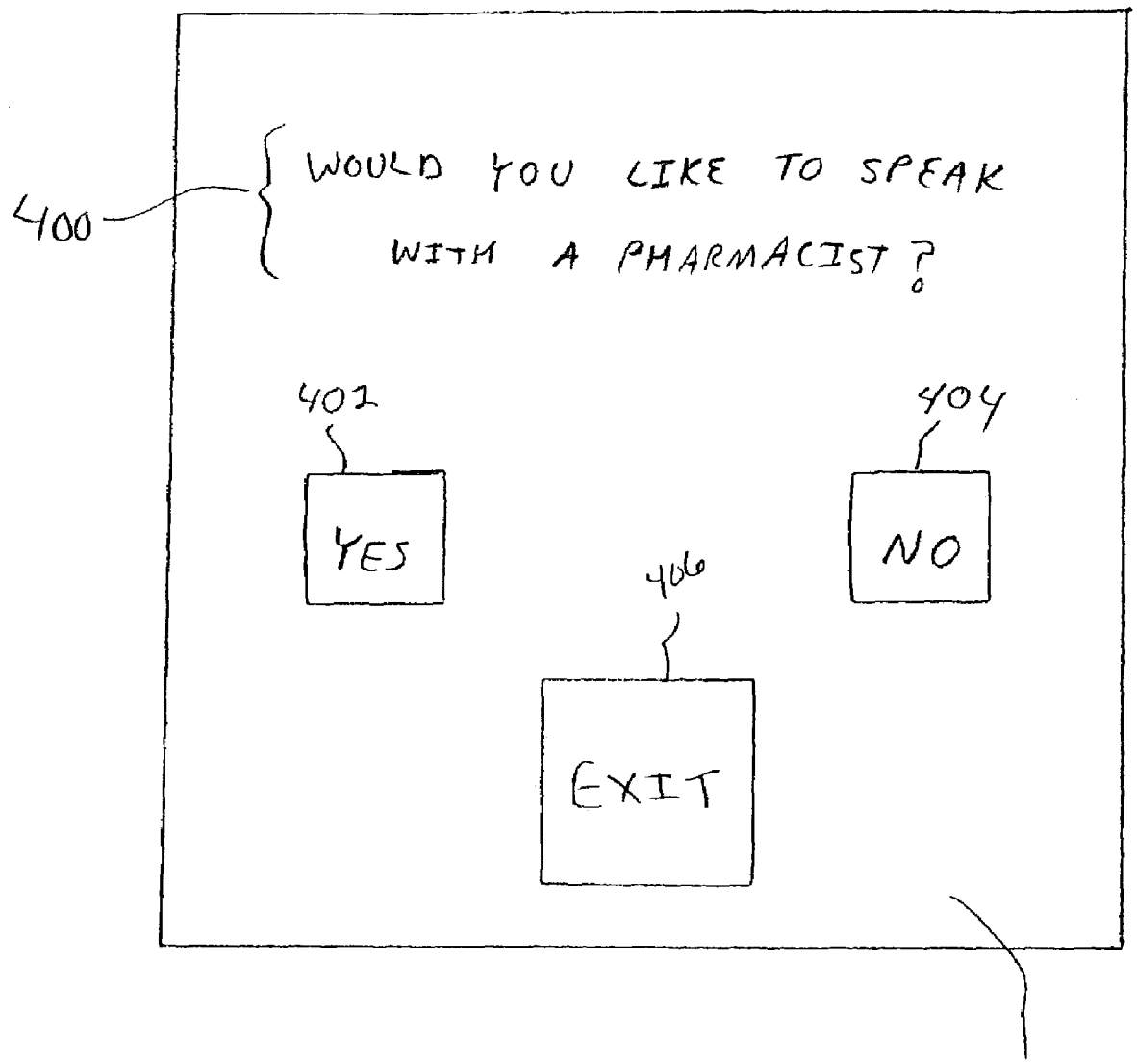
FIG. 4 is a second expanded view of the touch-screen of FIG. 1.

As shown in FIG. 2, if the patient opts to decline pharmaceutical information at step 206, the patient may be prompted with a second electronic message which comprises the question "Would you like to speak with a pharmacist?" or equivalent message. Referring to FIG. 4, there is shown the second electronic message on the touch screen 18 at bracket 400. If the patient wishes to speak with the pharmacist, the patient may interact with the pharmaceutical instruction system 10 by touching the "YES" icon at 402 and if the patient does not wish to speak with the pharmacist, the patient may touch the "NO" icon at 404. If the patient does not wish to speak with a pharmacist, the process may stop as indicated at step 208, wherein the instruction program ends and optionally resets.

The pharmaceutical instruction system 10 may also be configured to prompt the patient with the option of speaking with the pharmacist on each screen displayed to the patient during the pharmaceutical information session. In this manner, if the patient requires assistance from the pharmacist, the patient may select the appropriate area on the touch screen 18 and speak with the pharmacist at any time during the counseling session. Referring again to FIG. 3, the patient may also be provided with the opportunity to exit the pharmaceutical instruction system 10 at any time during the counseling session by touching an "EXIT" icon 306 on the touch screen 18. As illustrated in FIG. 4, the option to exit the instruction session may be displayed on each screen provided to the patient, such as at icon 406.

If the patient wishes to speak with the pharmacist by selecting the "YES" icon 402, the pharmaceutical instruction system 10 may communicate the action of the patient to the pharmacist with the notification device 28. As illustrated in FIG. 1, the notification device 28 is positioned within the pharmacist area 110 and allows the pharmacist to be alerted by the action of the patient. As illustrated, the notification device 28 is a computer display operatively connected to the pharmaceutical instruction system 10, but in alternative embodiments the notification device 28 may comprise a speaker, a light or any other suitable device for alerting the pharmacist or ancillary staff of the pharmacy. In an alternative embodiment, the pharmacist may be alerted by the ancillary staff of the pharmacy.

Since the pharmaceutical instruction system 10 described herein utilizes an interactive input, such as the touch-screen 18, patients are able to control the extent of pharmaceutical product information they wish to receive. In this manner, patients who may feel embarrassed to ask for information or help will be able to use the pharmaceutical instruction system 10 to receive the desired information. Alternatively, some patients may be intimidated by the pharmaceutical instruction system 10 and not feel comfortable using the pharmaceutical instruction system 10. In these instances, the pharmacist or ancillary staff member at the pharmacy may interact with the patient directly to ensure that the pharmaceutical information is communicated to the patient.

It is also within the scope of the present invention to provide an executable software program (hereinafter "software program") that controls the pharmaceutical instruction system 10. Since the pharmaceutical instruction system 10 employs a computer-based apparatus 22 to control the various components of the pharmaceutical instruction system 10, the software program may be designed to control the operation of the computer-based apparatus 22. In the illustrated embodiment, the computer-based apparatus 22 includes a central processing unit and a memory device wherein the software program is stored on the memory device of the computer-based apparatus 22. The memory device of the computer-based apparatus 22 may also be configured to store the pharmaceutical information such that the pharmaceutical information may be retrieved by the computer-based apparatus 22. The software program may be configured to instruct the central processing unit to collect data gathered by the bar-code scanner 12, generate the message "Would you like to receive information on using the pharmaceutical product?," display the message on the touch-screen display 18, receive data collected from the touch-screen display 18 in response to the patient touching the "YES" icon 302 or the "NO" icon 304, and controlling the touch-screen display 18, the printer 20, the headphones 26, the telephone receiver 30, the speaker 24 or combinations thereof to output the pharmaceutical information to the patient. In this manner, the central processing unit controls execution of the software program and, thus, the pharmaceutical information session.

The pharmaceutical instruction system 10 may also be implemented on an existing computer system. For example, if a pharmacy has an existing computer system, the pharmacy would be able to install the executable software program on the existing computer system and add the appropriate peripheral devices to form the pharmaceutical instruction system 10 of the present invention. In this manner, the central processing unit of the existing computer system would control the various devices of the pharmaceutical instruction system 10.

Although the illustrated embodiment has been described with the illustrated computer-based system, it will be apparent that other electronic systems may be used in place of, or in combination with, the computer-based pharmaceutical instruction system 10 described herein. For instance, a phone based or other electronically based voice system may be used to perform the method of FIG. 2. With the phone based system, the patient may be asked to input responses to prompted, audible digitized messages using the touch tone keypad of a telephone or by speaking into the telephone receiver 30 (as shown in FIG. 1) where a voice recognition system recognizes the voice, such that the patient is directed through a series of audible messages.

The method of providing counseling information of FIG. 2 may also be provided to a patient through the internet. For instance, the pharmacy may operate, a web-site where a patient would log on to the web-site after receiving the pharmaceutical product. In this manner, the patient may access the counseling information from their home. Instead of directly speaking with the pharmacist, the web-site based pharmaceutical information session may provide a direct link to an email address of the pharmacist where the patient may send an email message to the pharmacist to ask any desired question.

In addition to providing pharmaceutical information, the present invention enables the pharmacy to generate an electronic log of the pharmaceutical product being picked up and the pharmaceutical product information displayed to the patient. The current practice pharmacies use to log when a patient picks up a pharmaceutical product is to affix an adhesive label to a notebook and have the patient sign the adhesive label. The signed logs are typically stored for a period of about five years and may be viewed by third party administrators to ensure that pharmaceutical products were filled and picked up by patients. A typical pharmacy may fill hundreds of notebooks per year which may create storage problems. Accordingly, the pharmaceutical instruction system 10 of the present invention may be operatively configured to track and store the year, month, day, hour and minute of the patient picking up the pharmaceutical product and whether or not the patient opted to receive pharmaceutical product information or speak with the pharmacist. An electronic signature of the patient may also be facilitated and stored by employing an electronic signature capture device 32 as illustrated in FIG. 1. Devices which read and store electronic signatures are known and include, without limitation, back-lit Liquid Crystal Display (LCD) signature capture terminals and any other similar device capable of recognizing and storing electronic signatures. The electronically logged information may be stored on the memory device of the computer-based apparatus 22, stored on an external storage device such as an external hard drive, a floppy disk, a CD-disk or printed on a print medium for storage.

The present invention thus enables a patient to receive counseling information while helping to diminish the workload on the pharmacist. By employing the present invention, the pharmacist is able to focus attention to patients who require more detailed attention, while other patients, such as those obtaining refill prescriptions, are able to receive pharmaceutical product information and counseling information with the disclosed pharmaceutical instruction system 10. Further, if the patient receives pharmaceutical product information with the headphones 26 or telephone receiver 30, the patient is able to discretely receive the information without interrupting other patrons at the pharmacy or receive counseling which may be personal in nature without feeling embarrassed or uncomfortable.

Although the pharmaceutical instruction system 10 has been described in one particular embodiment regarding the distribution of information for pharmaceutical product medications, the invention is not meant to be so limited. The invention may also be used to provide information related to over the counter drugs, medical devices and other pharmaceutical products. Further, the invention may have utility in other professions where counseling or pharmaceutical product information is to be provided.

Having thus described certain illustrative embodiments of the present invention, it is to be understood that the invention defined by the appended claims is not to be limited by particular details set forth in the above description, as many apparent variations thereof are possible without departing from the spirit or scope thereof as hereinafter claimed.

What is claimed is:

1. A method for providing pharmaceutical information to a patient, said method comprising:
   dispensing a pharmaceutical product having an electronically identifiable tag associated with said pharmaceutical product;
   electronically reading said electronically identifiable tag of said pharmaceutical product to identify said pharmaceutical product;
   prompting said patient with a selective opportunity to accept or decline prescription counseling by interacting with an electronic input device;
   wherein said patient selects to accept said prescription counseling by step-wise interactively, retrieving electronically stored pharmaceutical information about said pharmaceutical product in increasingly detailed information comprising:
   special directions;
   precautions;
   other drug interactions;
   adverse side effects; and or
   actions to be taken in event a dose is missed; and
   electronically disclosing said stored pharmaceutical information visually and/or audibly counseling to said patient comprising:
      electronically prompting said patient with a first message, wherein said first message provides said patient with an interactive choice of accepting or declining said pharmaceutical counseling; and
      wherein said pharmaceutical counseling is electronically disclosed to said patient upon said patient interactively choosing to accept said pharmaceutical counseling, based upon said information derived from said electronic identification of said pharmaceutical product, or wherein no pharmaceutical information is electronically disclosed to said patient upon said patient interactively choosing to decline said pharmaceutical counseling; and
      a historical record is established for the patient counseling interaction.

2. The method according to claim 1, further comprising:
   electronically prompting said patient with a second message at each step of interactively retrieving electronically stored pharmaceutical information which provides said patient with an interactive option to speak with a pharmacist; and
   wherein said patient interactively interrupts retrieving electronically stored pharmaceutical information to accept or decline said option to speak with a pharmacist.

3. The method according to claim 2, further comprising electronically notifying said pharmacist of said option selected by said patient to speak with said pharmacist.

4. The method according to claim 1, wherein said electronic input device comprises a touch-screen display, a microphone or a keyboard.

5. The method according to claim 1, further comprising electronically creating an electronic log of said interaction of said patient.

6. The method according to claim 1, further comprising said patient providing a signature and electronically recording said signature of said patient.

7. The method according to claim 1, wherein electronically disclosing said stored pharmaceutical counseling further comprises an act selected from the group consisting of: electronically displaying said stored pharmaceutical counseling to said patient on an electronic visual display, printing said stored pharmaceutical counseling on a print medium, generating a voice message reciting said stored pharmaceutical counseling, and combinations thereof.

8. The method according to claim 1, wherein electronically prompting said patient with said first message is selected from the group consisting of: electronically displaying said first message to said patient on an electronic visual display, printing said first message on a print medium, generating a voice message reciting said first message, and combinations thereof.

9. The method according to claim 1, further comprising storing the patient's selection of accepting or declining the prescription counseling.

10. The method according to claim 1, wherein said prescription counseling complies with state law requirements for prescription counseling.

* * * * *